United States Patent [19]

Caruso et al.

[11] Patent Number: 4,965,351
[45] Date of Patent: Oct. 23, 1990

[54] 4-DEMETHOXY-4-AMINO-ANTHRACYCLINES

[75] Inventors: Michele Caruso; Antonino Suarato; Francesco Angelucci; Federico Arcamone, all of Milan, Italy

[73] Assignee: Farmitalia Carlo Erba S.R.L., Milan, Italy

[21] Appl. No.: 430,149

[22] Filed: Nov. 1, 1989

Related U.S. Application Data

[62] Division of Ser. No. 181,506, Apr. 14, 1988, abandoned.

[30] Foreign Application Priority Data

Apr. 21, 1987 [GB] United Kingdom ............... 8709353
Feb. 12, 1988 [GB] United Kingdom ............... 8803302

[51] Int. Cl.$^5$ ..................... C07H 15/24; A01N 43/04
[52] U.S. Cl. ..................................................... 536/6.4
[58] Field of Search ............................. 536/6.4; 514/34

[56] References Cited

U.S. PATENT DOCUMENTS

| | | | |
|---|---|---|---|
| 4,021,457 | 5/1977 | Kende et al. | 536/4.1 |
| 4,109,076 | 8/1978 | Henry | 536/4.1 |
| 4,348,388 | 9/1982 | Garland | 536/6.4 |
| 4,448,724 | 5/1984 | Cava et al. | 536/4.1 |

FOREIGN PATENT DOCUMENTS 0143323 6/1985 European Pat. Off.
0254484 1/1988 European Pat. Off.

OTHER PUBLICATIONS

I. L. Finar: "Organic Chemistry", 1954, Longmans, Green and Co., London, GB.

Primary Examiner—Ronald W. Griffin
Assistant Examiner—Pamela S. Webber
Attorney, Agent, or Firm—Oblon, Spivak, McClelland, Maier & Neustadt

[57] ABSTRACT

Anthracycline glycosides of the general formula (I):

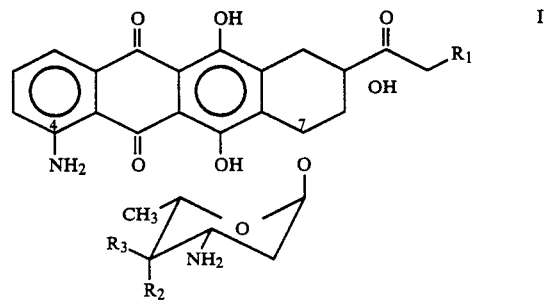

wherein $R_1$ represents a hydrogen atom or a hydroxyl group, one of $R_2$ and $R_3$ represents a hydrogen atom and the other of $R_2$ and $R_3$ represents a hydrogen atom or a hydroxyl group; and pharmaceutically acceptable acid addition salts thereof are antitumor agents. These glycosides may be prepared from a daunomycinone derivative of formula (II):

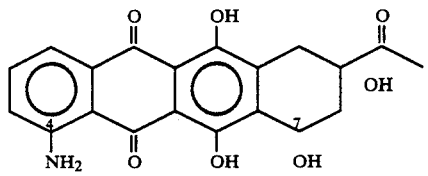

in which the 4-amino group is protected. 4-Demethoxy-4-amino-daunomycinone (II) and an earlier intermediate in its preparation, 4-demethoxy-4-amino-7-deoxy-daunomycinone (IX), can be diazotized followed by mild reduction to form 4-demethoxy-daunomycinone or 4-demethoxy-7-deoxy-daunomycinone respectively. 4-Demethoxy-daunomycinone can be converted into another antitumor anthracycline glycoside, 4-demethoxy-daunorubicin.

12 Claims, No Drawings

4-DEMETHOXY-4-AMINO-ANTHRACYCLINES

This is a division of application Ser. No. 07/181,506, filed on April 14, 1988, now abandoned.

The invention relates to anthracycline glycosides; to their preparation, to pharmaceutical compositions containing them and to intermediates for use in the preparation of the anthracycline glycosides.

The invention provides anthracycline glycosides having the general formula (I):

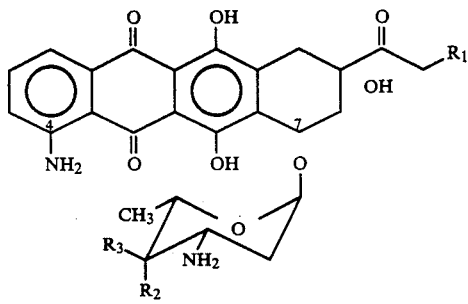

wherein $R_1$ represents a hydrogen atom or a hydroxyl group, one of $R_2$ and $R_3$ represents a hydrogen atom and the other of $R_2$ and $R_3$ represents a hydrogen atom or a hydroxyl group, and their pharmaceutically acceptable addition salts. Preferred salts are the hydrochloride salts. The compounds of formula (I) may be named as follows:

Ia: $R_1=R_3=H$; $R_2=OH$
  4-demethoxy-4-amino-daunorubicin
Ib: $R_1=R_2=OH$; $R_3=H$
  4-demethoxy-4-amino-doxorubicin
Ic: $R_1=R_2=H$; $R_3=OH$
  4-demethoxy-4-amino-4'-epi-daunorubicin
Id: $R_1=R_3=OH$; $R_2=H$
  4-demethoxy-4-amino-4'-epi-doxorubicin
Ie: $R_1=R_2=R_3=H$
  4-demethoxy-4-amino-4'-deoxy-daunorubicin
If: $R_1=OH$; $R_2=R_3=H$
  4-demethoxy-4-amino-4'-deoxy-doxorubicin The glycosides of formula (I) and their pharmaceutically acceptable addition salts are prepared by a process which comprises (i) reacting a protected derivative of a daunomycinone derivative of formula (II):

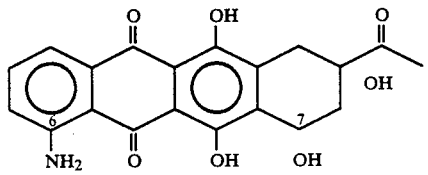

wherein the 4-amino group is protected, with a protected halosugar of formula (III)

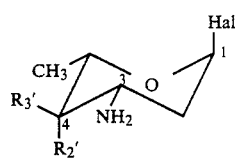

wherein one of $R'_2$ and $R'_3$ represents a hydrogen atom, the other of $R'_2$ and $R'_3$ represents a hydrogen atom or a protected hydroxy group, the 3-amino group is protected and Hal represent a halogen atom, and removing the protecting groups from the product thus-obtained such as to obtain an anthracycline glycoside of formula (I) wherein $R_1$ is hydrogen;

(ii) if desired, converting the said glycoside of formula (I) into a pharmaceutically acceptable salt thereof;

(iii) if desired, brominating the said glycoside of formula (I) or pharmaceutically acceptable salt thereof and hydrolysing the 14-bromo derivative thus-obtained so as to form the corresponding glycoside of formula (I) wherein $R_1$ is hydroxy; and (iv) if desired, converting the said glycoside of formula (I) wherein $R_1$ is hydroxy into a pharmaceutically acceptable salt thereof.

Preferably, in step (i) the protected derivative of the daunomycinone derivative of formula (II) is 4-demethoxy-4-N-trifluoroacetamido-daunomycinone. The protected halosugar is preferably a protected halosugar having the formula (IV):

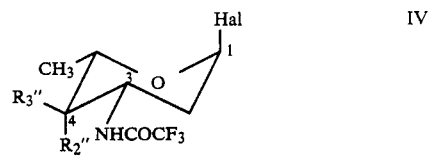

wherein one of $R''_2$ and $R''_3$ represents a hydrogen atom, the other of $R''_2$ and $R''_3$ represents a hydrogen atom or a trifluoroacetoxy group, and Hal is as defined above. Preferably Hal is a chlorine atom.

The condensation of 4-demethoxy-4-N-trifluoroacetamido-daunomycinone and the protected halosugar (IV) may proceed in the presence of silver triflate. The method described in U.S. Pat. No. 4,107,423 may be used, giving (7S,9S)-O-trifluoroacetyl protected derivatives of the a-glycosides. The 4-demethoxy-4-N-trifluoroacetamido-daunomycinone can be dissolved in anhydrous methylene chloride with reaction proceeding at 5° to 10° C. The N-protecting trifluoroacetyl groups may be removed by mild alkaline treatment.

Preferably, an anthracycline glycoside of formula (I) wherein $R_1$ is hydrogen is isolated in step (ii) as its hydrochloride. Subsequent treatment of the resultant 4-demethoxy-4-amino-daunorubicin derivatives, in accordance with the method described in U.S. Pat. No. 4,067,969, affords the corresponding 4-demethoxy-4-amino-doxorubicins in step (iii). Hydrolysis may be effected with sodium formate. In step (iv), a resultant anthracycline glycoside of formula (I) wherein $R_1$ is hydroxy preferably is isolated as its hydrochloride.

The daunomycinone derivative of formula (II) and protected derivatives thereof wherein the 4-amino group is protected also form part of the invention. These compounds may be prepared by a process which comprises:

(a) removing by hydrogenolysis the 7α-hydroxyl group of carminomycinone of formula (V):

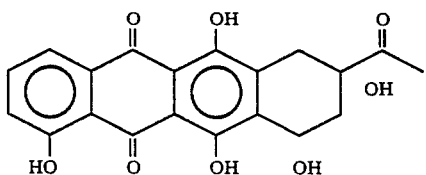

(b) reacting the resultant 4-demethyl-7-deoxy-daunomycinone of formula (VI):

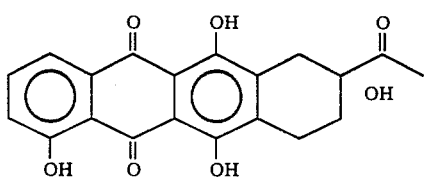

with 4-fluorobenzensulfonyl chloride in the presence of N,N-diisopropylethylamine and a catalytic amount of 4-dimethylaminopyridine;

(c) reacting the resultant 4-demethoxy-4-O-[4-fluorobenzensulfonyl]-7-deoxy-daunomycinone of formula (VII):

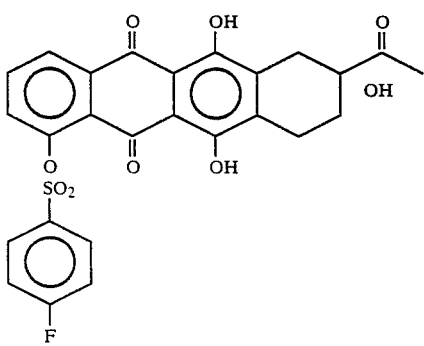

with benzylamine;

(d) removing the benzyl group from the resultant 4-demethoxy-4-benzylamino-7-deoxy-daunomycinone of formula (VIII):

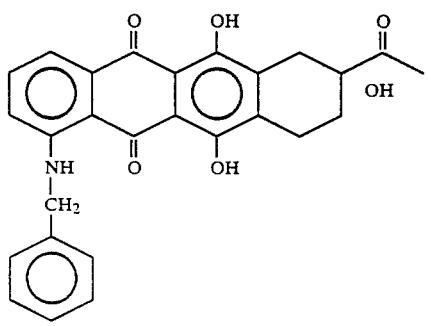

by catalytic hydrogenation;

(e) protecting the 4-amino group of the resultant 4-demethoxy-4-amino-7-deoxy-daunomycinone of formula (IX):

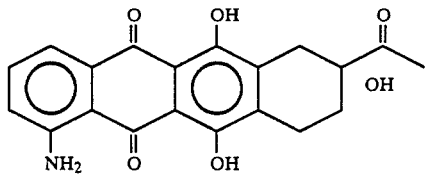

(f) reintroducing the 7α-hydroxy group into the resultant compound of formula (X):

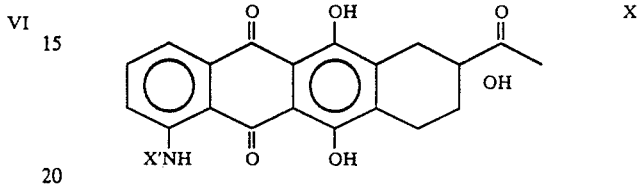

wherein X' represents the amino protecting group, thereby obtaining a protected derivative of formula (XI) of a daunomycinone derivative of formula (II):

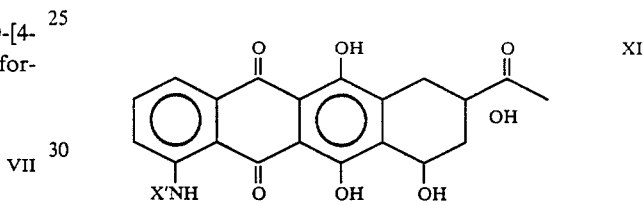

wherein X' is defined above; and (g) if desired, removing the 4-amino protecting group from the protected derivative of formula (XI), thereby obtaining the daunomycinone derivative of formula (II):

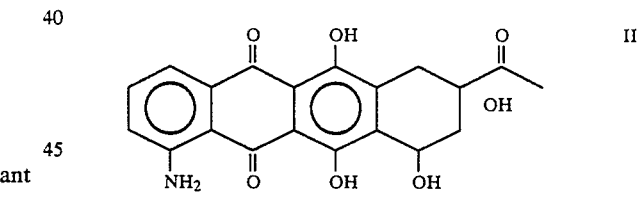

This process is illustrated in Scheme I below. The starting compound for the process is the natural carminomycinone (V). The sulfonylation reaction, step (b), leads only the substituted C-4-O-sulfonyl derivative (VII), leaving the C-6-OH and C-11-OH unaffected. It should be stressed that this unexpected selectivity has been achieved only under the conditions described herein.

Scheme I

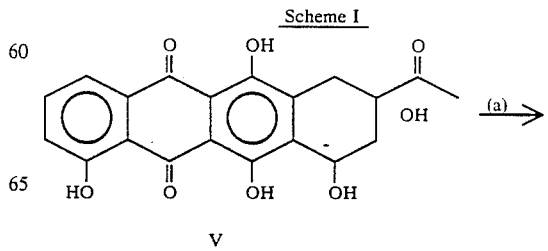

-continued
Scheme I

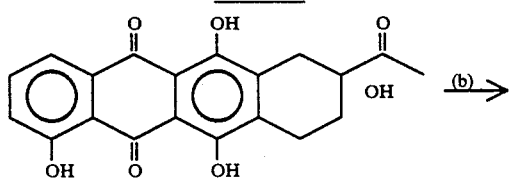
VI

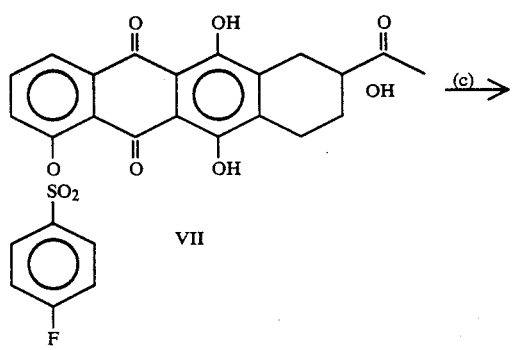
VII

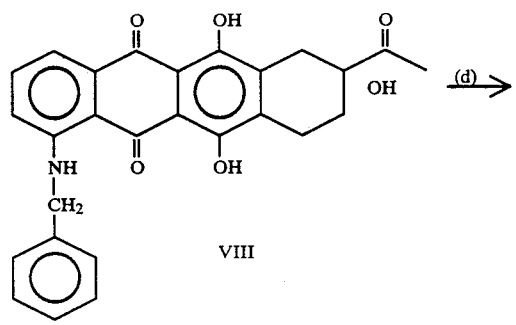
VIII

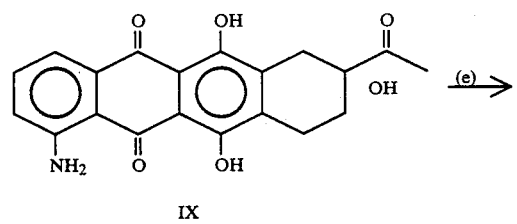
IX

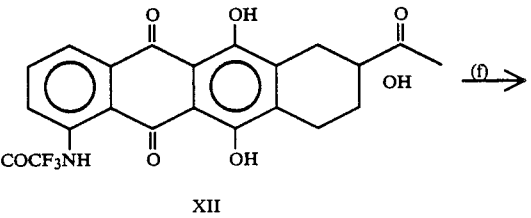
XII

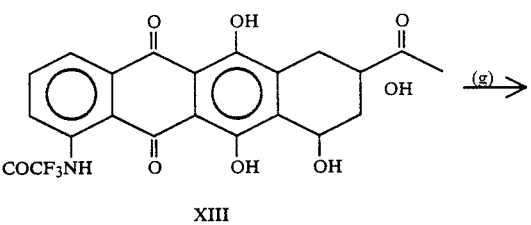
XIII

-continued
Scheme I

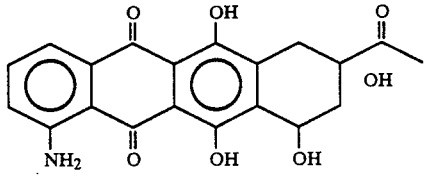
II

Reaction (c) is a new one in anthracycline chemistry, probably due to the withdrawing effect both of the quinone moiety and of the 4-fluoro-benzensulfonyl group at the position C-4. Preferably, the reaction is effected in tetrahydrofuran at room temperature. Step (e) is preferably effected with trifluoroacetic anhydride. Preferably, therefore X' represents a trifluoroacetyl group in formulae (X) and (XI). Step (f) may be performed according to the method described by C. M. Wong et al., Can. J. Chem., 51, 446 (1973). Preferably, it is effected by protecting the 13-keto group of a 4-demethoxy-4-(protected amino)-7-deoxy-daunomycinone compound of formula (XII):

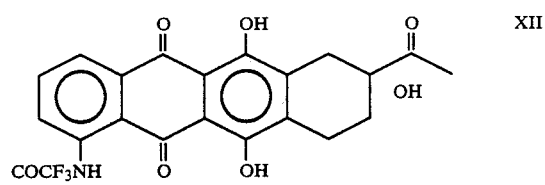

by treatment with ethylene glycol; brominating the resultant compound at the 7-position; and hydrolysing the 7-bromo and 13-ketal groups to give 4-demethoxy-4-N-trifluoroacetamido-daunomycinone of formula (XIII):

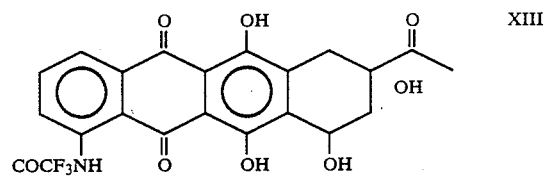

Bromination is generally achieved by treatment with bromine or N-bromosuccinimide in the presence of 2,2'-azo-bis(isobutyronitrile).

The intermediates of formula (II) and (IX) are also useful for the preparation of 4-demethoxy-7-deoxy-daunomycinone or 4-demethoxy-daunomycinone. The intermediate 4-demethoxy-4-amino-7-deoxy-daunomycinone of formula (IX) forms an additional aspect of the invention, as does its preparation according to steps (a) to (d) above. 4-Demethoxy-7-deoxy-daunomycinone can be converted into 4-demethoxy-daunomycinone. Further antitumor anthracycline glycosides can be prepared from 4-demethoxy-daunomycinone.

According to the present invention, there therefore further is provided a process for preparing 4-demethoxy-7-deoxy-daunomycinone or 4-demethoxy-daunomycinone of formula (XIV):

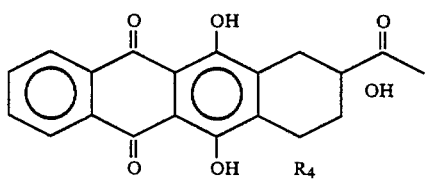

XIV in which $R_4$ represents hydrogen or hydroxy, which process comprises diazotising the 4-amino group of 4-demethoxy-4-amino-7-deoxy-daunomycinone or 4-demethoxy-4-amino-daunomycinone of formula (XV):

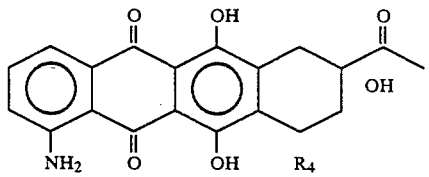

XV in which $R_4$ is as defined above, and reducing under mild conditions the diazonium compound thus-formed.

Anthracyclinones bearing an amino group at position C-4 are therefore transformed into their corresponding desamino derivatives. The starting compounds are 4-demethoxy-4-amino-7-deoxy-daunomycinone (IX(XVa, R=H)) and 4-demethoxy-4-amino-daunomycinone (II (XVb, R=OH)). The removal of the 4-amino group, via diazotisation and mild reduction, leads to the well known 4-demethoxy-7-deoxy-daunomycinone (XIVa, R=H) or 4-demethoxy-daunomycinone (XIVb, R=OH). As shown in Scheme II, diazotisation is preferably effected using aqueous sodium nitrite. The mild reduction is preferably effected using hypophosphorous acid.

Scheme II

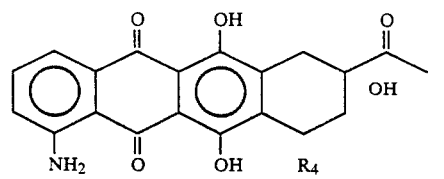

(1) aq NaNO₂
(2) Hypophosphorous acid

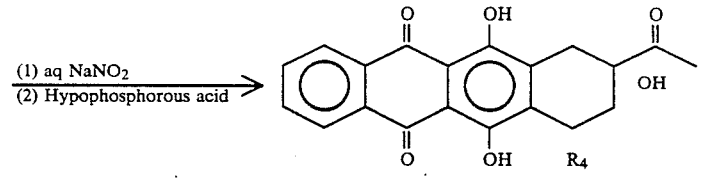

Compound XVa in which $R_4$=H can be easily transformed into compound XVb in which $R_4$=OH by standard methods. Preferably, the 4-demethoxy-4-amino-7-deoxy-daunomycinone (XVa) or 4-demethoxy-4-amino-daunomycinone (XVb), dissolved in aqueous 37% hydrochloric acid, is reacted at a temperature of from 0° to 5° C.⁻ and for 1 hour with an aqueous solution of sodium nitrite and, subsequently, for 5 hours at room temperature under vigorous stirring with an aqueous solution of 50% hypophosphorous acid, the reaction mixture is extracted with methylene dichloride and the solvent is removed under reduced pressure.

4-Demethoxy-7-deoxy-daunomycinone (XIVa) may be converted into 4-demethoxy-daunomycinone (XIVb) by introducing a hydroxy group at the 7-position. This can be achieved according to the invention by bromination of the 7-position, for example by bromine or N-bromo-succinimide (NBS), followed by treatment with alkali or with silver acetate or methanolysis of the acetate thus formed.

4-Demethoxy-daunomycinone (XIVb) is the aglycone moiety of the useful antitumor drug 4-demethoxy-daunorubicin (XVI). Accordingly, the present invention further provides a process for preparing 4-demethoxy-daunorubicin of formula (XVI):

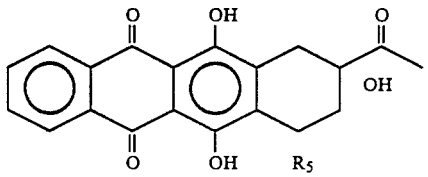

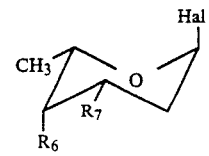

$R_5 =$ or a pharmaceutically acceptable salt thereof; which process comprises reacting 4-demethoxy-daunomycinone, which is represented by formula (XIV) in which $R_4$ is hydroxy and which has been prepared from 4-demethoxy-4-amino-daunomycinone by a process according to the invention, with an appropriate sugar derivative and, if desired, converting the 4-demethoxy-daunorubicin thus-obtained into a pharmaceutically acceptable salt thereof.

The sugar derivative may have the formula (XVII):

wherein Hal represents a halogen atom, $R_6$ represents a protected hydroxy group and $R_7$ represents a protected amino group. The protecting groups are removed after reaction with 4-demethoxy-daunomycinone. Preferably Hal is a chlorine atom. The hydroxy group may be protected by a trifluoroacetyl group. The amino group may be protected by a trifluoroacetyl group also.

The invention also provides pharmaceutical compositions comprising a pharmaceutically acceptable carrier or diluent and an anthracycline glycoside of formula (I) or a pharmaceutically acceptable salt thereof, or an anthracycline glycoside of formula (XVI) or a pharmaceutically acceptable salt thereof which has been prepared as above.

Conventional formulations, carriers and diluents may be used. The compositions for administration to a patient comprise a therapeutically effective amount of a glycoside. Thus, a therapeutically effective amount of a glycoside can be administered, by a conventional route, to a human patient.

The glycosides are antitumor agents. The activity of a representative compound of formula (I), 4-demethoxy-4-amino-daunorubicin (Ia), has been assessed by comparing its in vitro cytotoxicity against that of daunorubicin (DNR) in human colon adenocarcinoma cells sensitive (LoVo) or resistant (LoVo/DX) to doxorubicin. The results are shown in Table 1:

TABLE 1

| Colony inhibition test after 4 h. treatment. | | |
| --- | --- | --- |
| Compound | LoVo $ID_{50}$ (ug/ml) | LoVo/DX $ID_{50}$ (ug/ml) |
| Ia | 0.7 | 99 |
| DNR | 50.3 | 1805 |

The in vivo activities of (Ia) and DNR against disseminated Gross leukaemia in mice also determined. The results are shown in Table 2:

TABLE 2

| Treatment i.v on day 1 after tumor inoculum | | | |
| --- | --- | --- | --- |
| Compound | mg/Kg | T/C % | TOX |
| DNR | 10 | 133 | 0/10 |
| | 15 | 167 | 0/10 |
| | 22.5 | 200 | 1/10 |
| Ia | 1.6 | 183 | 0/10 |
| | 1.9 | 192 | 0/10 |
| | 2.29 | 200 | 1/10 |

TC % represents,
TOX represents toxic death

The following Examples illustrate the invention.

EXAMPLE 1

4-Demethyl-7-deoxy-daunomycinone (VI)

1.5 g of 4-demethyl-daunomycinone (V) dissolved in a mixture of 100 ml of dioxane and 100 ml of ethanol was hydrogenated in the presence of 0.3 g of 5% Pd-BaSo4 at room temperature for 3 hours. After filtration the solvent was removed in vacuo and 4-demethyl-7-deoxy-daunomycinone (VI) was recovered in almost quantitative yield. TLC on kieselgel F254 (Merck) using Toluene:Acetone (9:1 by volume) Rf=0.30.

EXAMPLE 2

4-Demethyl-4-O-(4-fluoro-benzensulfonyl)-7-deoxy-daunomycinone (VII)

To a stirred solution of 1.0 g of 4-Demethyl-7-deoxy-daunomycinone (VI) in 200 ml of anhydrous methylene dichloride containing 0.52 ml of N,N-diisopropylethylamine and a catalytic amount of 4-dimethylaminopyridine, at room temperature, was added 0.52 g of 4-fluoro-benzensulfonylchloride. After 30 minutes the transformation was complete and the reaction mixture was washed with 0.1N aqueous hydrochloric acid, then water.

The organic solution was dried over anhydrous sodium sulphate, the solvent filtered off was and removed in vacuo. The crude product was picked up with a little toluene and crystallized to give 0.6 g of pure 4-demethyl-4-O-sulfonate derivative of formula IV. Others 0.3 g of product was recovered by purification of the liquor through a chromatographic column using as eluant a mixture of toluene/acetone. Yield 80%.

TLC on Kieselgel F254 (Merck) using Toluene:Acetone (9:1 by volume) Rf=0.26.

FDMS [M·+] 526.
UV$\lambda_{max}$ (MeOH): 524, 490 nm.
1HNMR (200 MHz, CDCl3δ: 13.43, 13.36 (s, 2H, 11-OH, 6-OH), 8.38 (dd, J=1.3, 7.9 Hz, 1H, 1-H) 8.02 (m, 2H,

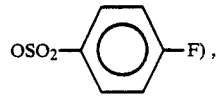

7.80 (dd, J=7.9, 8.1 Hz, 1H 2-H), 7.62 (dd, J=1.3, 8.1 Hz, 1H, 3-H), 7.23 (m, 2H,

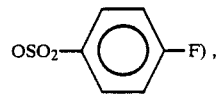

3.77 (s, 1H, 9-OH), 3.1–2.8 (m, 4H, 7-CH2, 10-CH2), 2.38 (s, 3H, COCH3), 2.0–1.9 (m, 2H, 8-CH2).

EXAMPLE 3

4-Demethoxy-4-benzylamino-7-deoxy-daunomycinone (VIII)

0.8 g of compound VII was dissolved with 100 ml of tetrahydro furane and 0.5 ml of benzylamine was added.

The mixture was kept at 40° C. for 36 hrs under stirring, then 50 ml of 1N aqueous hydrochoric acid and 100 ml of methylene dichloride were added.

The organic phase was washed twice with water and dried over anhydrous sodium sulphate.

The solvent was removed in vacuo. The crude product was chromatographed by flash-chromatography, using as eluting solvent a mixture of toluene and acetone, to give 0.48 g of the 4-demethoxy-4-benzylamino-7-deoxy-daunomycinone (VIII). Yield 69%.

TLC on Kieselgel plate F254 (Merck) using Toluene:Acetone (9:1 by volume) Rf=0.28.

FDMS [M·+] 457.
UV$\lambda_{max}$ (MeOH): 548 nm.
1HNMR (200 MHz, CDCl3) δ: 13.58 (s, 2H, 6-OH, 11-OH), 9.86 (t, J=5.7 Hz, 1H, N$\underline{H}$-CH2Ph), 7.64 (d, J=7.3 Hz, 1H, 1-H), 7.49 (dd, J=7.3, 8.3 Hz, 1H, 2-H), 7.4–7.2 (m, 5H, NHCH2P$\underline{h}$), 7.00 (d, J=8.3 Hz, 1H, 3-H), 4.60 (d, J=5.7 Hz, 2H, NHC$\underline{H_2}$Ph), 3.1–2.9 (m, 4H, 10-CH2, 7-CH2), 2.37 (s, 3H, $\overline{COCH_3}$), 2.0–1.9 (m, 2H, 8-CH2).

EXAMPLE 4

4-Demethoxy-4-amino-7-deoxy-daunomycinone (IX)

0.45 g of 4-demethoxy-4-benzylamino-7-deoxy-daunomycinone (VIII), was dissolved with a mixture of 40 ml of ethanol, 20 ml of acetic acid and 0.4 ml of 37% aqueous hydrochloric acid.

0.2 g of 5% Pd/BaSO4 catalyst was added and the mixture was hydrogenated at 1 Atm. for 1 hr at room temperature. After that the catalyst was removed by filtration and the solvent evaporated in vacuo.

The crude product was chromatographed by flash chromatography using as eluent a mixture of toluene and acetone to give 0.2 g (yield 75%) of 4-demethoxy-4-amino-7-deoxy-daunomycinone (IX).

TLC on Kieselgel plate F254 (Merck) using Toluene:Acetone (9:1 by volume) Rf=0.17.

FDMS [M·+] 367.
UV$\lambda_{max}$ (MeOH): 536, 508 nm.

1HNMR (200 MHz, CDCl$_3$)δ: 13.62, 13.55 (s, 2H, 11-OH, 6-OH), 7.64 (d, J=7.7 Hz, 1-H), 7.46 (dd, J=7.7, 8.3 Hz, 1H, 2-H), 6.93 (d, J=8.3 Hz, 1H, 3-H), 6.8–7.0 (broad signal, 2H, NH$_2$), 3.83 (s, 1H, 9-OH), 3.1–2.8 (m, 4H, 7-CH$_2$, 10-CH$_2$), 2.37 (s, 3H, COCH$_3$), 2.0–1.9 (m, 2H, 8-CH$_2$).

EXAMPLE 5

4-Demethoxy-4-N-trifluoroacetamido-7-deoxy-daunomycinone (XII)

0.2 g of 4-demethoxy-4-amino-7-deoxy-daunomycinone (IX), was dissolved in 20 ml of anhydrous methylene dichloride, cooled at 0° C. and 0.3 ml of trifluoroacetic anhydride added. After 10 minutes aqueous sodium hydrogen carbonate was added.

The organic phase was washed twice with water and separated off, dried over anhydrous sodium sulphate. The solvent was removed in vacuo to give a quantitative yield of compound XII.

TLC on Kieselgel F254 (MercK) using Toluene Acetone (9:1 by volume) Rf=0.32.

EXAMPLE 6

4-Demethoxy-4-N-trifluoroacetamido-daunomycinone (XIII)

A suspension of 0.2 g of compound XII in 15 ml of benzene and 0.5 ml of ethylene glycol was refluxed for 4 hr in presence of 0.015 g of p-toluensulfonic acid using a Dean-Stark apparatus.

The mixture was cooled, washed with aqueous sodium hydrogen carbonate and water, then was evaporated to dryness to give 0.2 g of the expected ketal.

The latter was dissolved in 125 ml of methylene dichloride at 40° C. and was treated with bromine (1.7 ml of 0.6M solution in methylene dichloride) in presence of 0.25 g of 2,2'-azobisisobutironitrile.

After 3 hr the mixture was cooled and extracted with aqueous sodium hydrogen carbonate, then was washed twice with methylene dichloride and the solvent removed in vacuo. This residue was dissolved in 3 ml of trifluoroacetic acid and 0.3 ml of water at 0° C. and stirred for 1 hr, then extracted with methylene dichloride.

The organic phase was washed with aqueous sodium hydrogen carbonate and water. The solvent was filtered off, dried over anhydrous sodium sulfate and evaporated in vacuo to give 0.1 g of 4-demethoxy-4-N-trifluoroacetamido-daunomycinone (XIII), yield 48%.

TLC on Kieselgel plate F 254 (Merck) using CH$_2$Cl$_2$ Acetone (95:5 by volume) Rf=0.23.

FDMS [M·+] 479.

EXAMPLE 7

4-Demethoxy-4-amino-daunomycinone (II)

0.1 g of the 4-amino protected derivative XIII was poured in a mixture of 20 ml of methanol and 10 ml of aqueous sodium hydrogen carbonate and stirred for 1 hour, then was added with aqueous hydrochloric acid and methylene dichloride. The organic layer was separated and washed with water, the solvent was removed in vacuo to give 0.8 g of 4-demethoxy4-amino-daunomycinone (II).

TLC on Kieselgel plate F 254 (Merck) using CH$_2$Cl$_2$ (95:5 by volume) Rf=0.10.

FDMS [M·+] 383.

1HNMR (200 MHz, CDCl$_3$)δ: 14.00 (s, 1H, 6-OH), 13.52 (s, 1H, 11-OH), 7.64 (d,J=8.0 Hz, 1H, 1-H), 7.46 (t, J=8.0 Hz, 1H, 2-H), 6.93 (d, J=8.0 Hz, 1H, 3-H), 6.80 (broad, 2H, 4-NH$_2$), 5.32 (ddd, J=2.0, 4.8, 4.8 Hz, 1H, 7-H), 4.54 (s, 1H, 9-OH), 3.74 (d, J=4.8 Hz, 1H, 7-OH), 3.17 (dd, J=2.0, 19.0 Hz, 1H, 10e-H), 2.92 (d, J=19.0 Hz, 1H, 10ax-H), 2.45 (s, 3H, COCH$_3$), 2.35 (ddd, J=2.0, 2.0, 15.0 Hz, 1H, 8e-H, 2.14 (dd, J=4.8, 15.0 Hz, 1H, 8ax-H).

EXAMPLE 8

4-demethoxy-4-amino-daunorubicin (Ia)

0.08 g of 4-demethoxy-4-N-trifluoroacetamido-daunomycinone (XIII), prepared as described in Example 6, was dissolved in anhydrous methylene dichloride and the solution was cooled to 5°–10° C. A solution of 0.024 g of 1-chloro-N,O-ditrifluoroacetyl-daunosamine, prepared following the procedure described in Cancer Chemotherapy Reports, Part 3, Vol. 6, No. 2, p. 123, in diethyl ether and a solution of 0.150 g of silver trifluoromethanesulphonate in methylene dichloride were added simultaneously and rapidaly under vigorous stirring.

After 5 minutes, a further 0.070 g of silver trifluoromethane sulphonate were added and after 5 minutes the reaction was quenched with collidine.

The mixture was filtered, washed with a satured aqueous solution of sodium hydrogen carbonate and with water, dried and concentrate under vacuum.

The residue was chromatographed on a column of silica gel eluting with methylene dichloride, to give 4-demethoxy-4-N-trifluoroacetamido-N-trifluoroacetyl-daunorubicin (Ia).

The compound was dissolved in 10 ml of acetone and treated with 30 ml of 0.1N aqueous sodium hydroxide at 0° C. for 3 hours. Then to the solution was added 0.1N aqueous hydrochloric acid to adjust the pH to 4.5 and the aglycone were eliminated by extraction with methylene dichloride. Then the aqueous solution was adjusted to pH 8.6 and extracted with methylene dichloride, dried over anhydrous sodium sulphate, concentrated to a small volume and acidified to pH 4.5 with 0.1N methanolic hydrogen chloride to give the title compound as its hydrochloride.

EXAMPLE 9

4-demethoxy-4-amino-doxorubicin (Ib)

Following the process described in U.S. Pat. No. 3,803,124 and using as starting material 4-demethoxy-4-amino-daunorubicin, prepared as described in Example 8, the title compound was isolated as the hydrochloride.

EXAMPLE 10

Preparation of 4-demethoxy-7-deoxy-daunomycinone (XIVa)

1.78 g (5 mmol) of 4-demethoxy-4-amino-7-deoxy-daunomycinone (IX) dissolved with 75 ml of aqueous 37% hydrochloric acid, was cooled at 0°–5° C. and 75 ml of an aqueous solution containing 0.6 g of sodium nitrite is added. The mixture is stirred for one hour at 0°–5° C. Then 75 ml of an aqueous solution of 50% hypophosphorous acid is added and the mixture is kept at room temperature for five hours under vigorous stirring.

The solution is diluted with 200 ml of water and extracted with methylene dichloride. The organic layer is separated off, dried over anhydrous sodium sulphate and the solvent is removed under reduced pressure to give a quantitative yield (1.7 g) of 4-demethoxy-7- deoxy-daunomycinone (XIVa), analytically compared with a standard sample.

EXAMPLE 11

Preparation of 4-demethoxy-daunomycinone (XIVb)

1.86 g (5 mmol) of 4-demethoxy-4-amino-daunomycinone (II) are transformed into the corresponding 4-demethoxy-daunomycinone (XIVb) following the method above described. Yield: 1.8 g of compound XIVb analytically compared with a standard sample.

We claim:

1. A daunomycinone of formula (II)

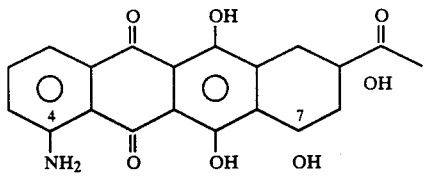

or a 4-protected amino derivative thereof.

2. The daunomycinone of claim 1, wherein said compound is 4-demethoxy-4-N-trifluoroacetamidodaunomycinone.

3. A process for the preparation of a daunomycinone of formula (IX)

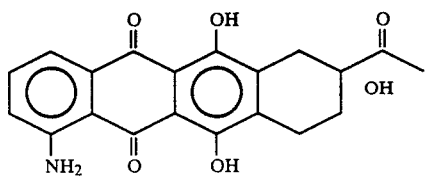

comprising the steps of:

(a) removing by hydrogenolysis, the 7α-hydroxyl group of a carminomycinone of formula (V)

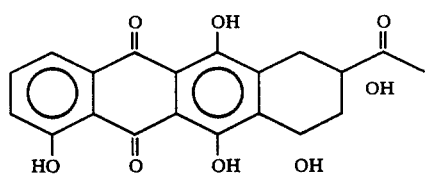

(b) reacting the resulting 4-demethyl-7-deoxy-daunomycinone of formula (VI)

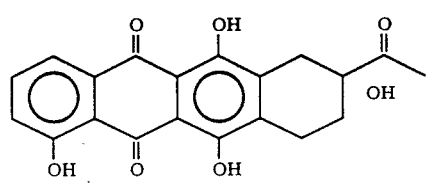

with a 4-fluorobenzenesulfonyl chloride in the presence of N,N-diisopropylethylamine and a catalytic amount of 4-dimethylaminopyridine, (c) reacting the resulting 4-demethoxy-4-O-[4-fluorobenzenesulfonyl]-7-deoxy-daunomycinone of formula (VII)

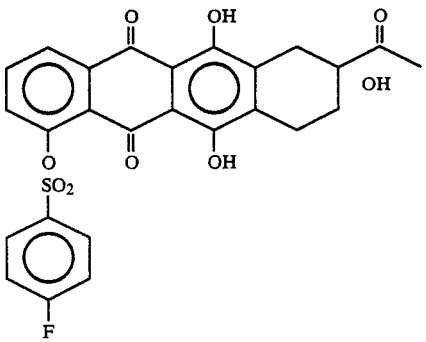

with benzylamine, (d) removing the benzyl group from the resulting 4-demethoxy-4-benzylamino-7-deoxy-daunomycinone of formula (VIII)

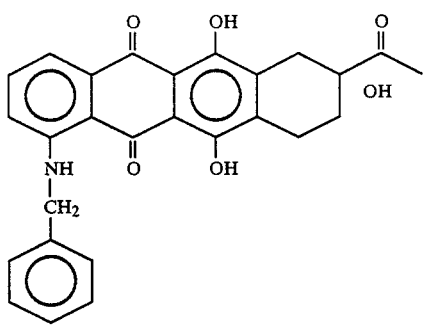

by catalytic hydrogenation.

4. The process of claim 3, further comprising:

(e) protecting the 4-amino group of the 4-demethoxy-4-amino-7-deoxy-daunomycinone of formula (IX) resulting from step (d)

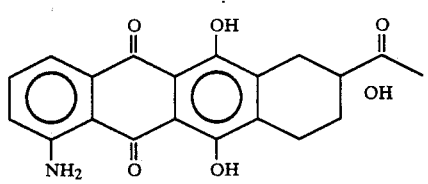

(f) reintroducing the 7α-hydroxy group into the resulting compound of formula (X)

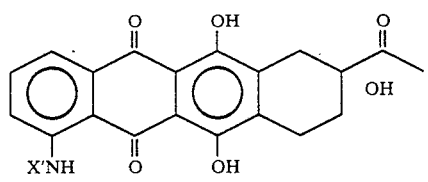

wherein X' is an amino-protecting group, thereby obtaining a protected derivative of formula (XI)

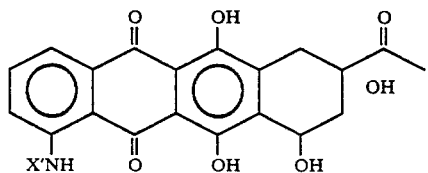

wherein X' is as defined above.

5. The process of claim 4, further comprising:

(g) removing the 4-amino protecting group from the protected derivative of formula (XI) thereby obtaining a daunomycinone derivative of formula (II)

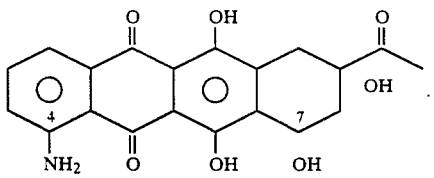

6. The process of claim 4, wherein step (e) is effected by treatment of trifluoroacetic anhydride.

7. The process of claim 4, wherein step (f) is effected by protecting the 13-keto group of a 4-demethoxy-4-(protected amino)-7-deoxy-daunomycinone of formula (XII)

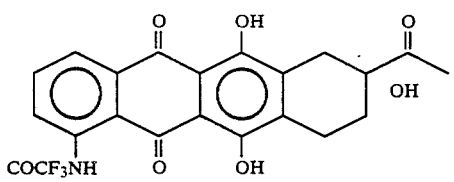

by treatment with ethylene glycol, brominating the resulting compound at the 7-position, and hydrolyzing the 7-bromo and 13-ketal groups to give 4-demethoxy-4-N-trifluoroacidamido-daunomycinone of formula (XIII)

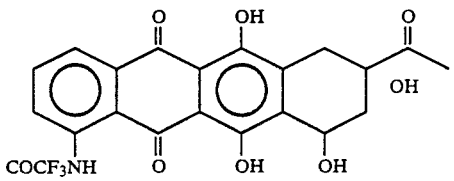

8. 4-Demethoxy-4-amino-7-deoxy-daunomycinone.

9. A process for preparing 4-demethoxy-7-deoxy-daunomycinone or 4-deoxy-daunomycinone of formula (XIV)

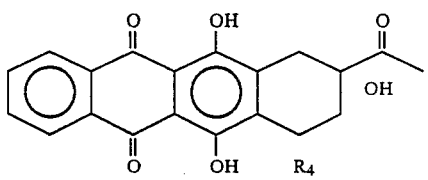

wherein $R_4$ is hydrogen or hydroxy, comprising the steps of:
  diazotizing the 4-amino group of 4-demethoxy-4-amino-7-deoxy-daunomycinone or 4-demethoxy-4-amino-daunomycinone of formula (XV)

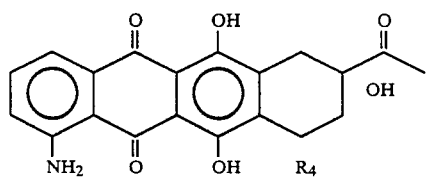

wherein $R_4$ is as defined above, and reducing the resulting diazonium compound.

10. The process of claim 9, wherein said reducing step is effected using hypophosphorus acid.

11. A process for the preparation of 4-demethoxy-4-daunomycinone of formula (XIV) where $R_4$ is hydroxy, which comprises:

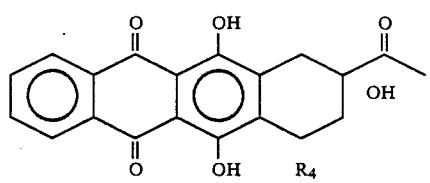

brominating the 7-position of 4-demethoxy-7-deoxy-daunomycinone of formula (XIV) wherein $R_4$ is hydrogen, followed by treatment with alkali or with silver acetate followed by methanolysis.

12. The process of claim 11, wherein said brominating step is conducted using bromine or N-bromosuccinimide.

* * * * *